United States Patent [19]
Strickland

[11] Patent Number: 5,218,957
[45] Date of Patent: * Jun. 15, 1993

[54] MULTI-LAYERED TRANSTRACHEAL CATHETER

[75] Inventor: Richard D. Strickland, Sandy, Utah

[73] Assignee: Ballard Medical Products, Draper, Utah

[*] Notice: The portion of the term of this patent subsequent to Apr. 6, 2010 has been disclaimed.

[21] Appl. No.: 600,435

[22] Filed: Oct. 19, 1990

[51] Int. Cl.$^5$ .............................. A61M 16/00
[52] U.S. Cl. .................... 128/200.26; 128/207.14
[58] Field of Search .............. 128/200.26, 207.14, 128/207.15, 207.29

[56] References Cited

U.S. PATENT DOCUMENTS

| | | | |
|---|---|---|---|
| 2,786,469 | 3/1957 | Cohen | 128/200.26 |
| 2,991,787 | 7/1961 | Shelden et al. | 128/207.29 |
| 3,039,469 | 6/1962 | Fountain | 128/200.26 |
| 3,225,767 | 12/1965 | Smith | 128/200.26 |
| 3,319,622 | 5/1967 | Shiner | 128/2 |
| 3,788,305 | 1/1974 | Schreiber | 128/2 F |
| 3,948,273 | 4/1976 | Sanders | 128/207.15 |
| 4,033,353 | 7/1977 | La Rosa | 128/351 |
| 4,037,605 | 7/1977 | Firth | 128/351 |
| 4,072,146 | 2/1978 | Howes | 128/2.05 D |
| 4,211,741 | 7/1980 | Ostoich | 264/173 |
| 4,235,229 | 11/1980 | Ranford et al. | 128/207.17 |
| 4,239,042 | 12/1980 | Asai | 128/207.29 |
| 4,239,042 | 12/1980 | Asai | 128/214.4 |
| 4,344,436 | 8/1982 | Kubota | 128/350 R |
| 4,385,635 | 5/1983 | Ruiz | 128/658 |
| 4,416,273 | 11/1983 | Grimes | 128/207.16 |
| 4,434,963 | 3/1984 | Russell | 251/7 |
| 4,525,156 | 6/1985 | Benusa et al. | 604/28 |
| 4,586,691 | 5/1986 | Kozlow | 251/7 |
| 4,596,563 | 6/1986 | Pande | 604/264 |
| 4,622,968 | 11/1986 | Persson | 128/200.26 |
| 4,627,433 | 12/1986 | Lieberman | 128/207.16 |
| 4,637,389 | 1/1987 | Heyden | 128/207 |
| 4,641,646 | 10/1987 | Schultz et al. | 128/207.14 |
| 4,649,913 | 3/1987 | Watson | 128/207.14 |
| 4,669,463 | 6/1987 | McConnell | 128/207.14 |
| 4,683,879 | 8/1987 | Williams | 128/200.26 |
| 4,716,901 | 1/1988 | Jackson et al. | 128/200.26 |
| 4,838,255 | 6/1989 | Lambert | 128/202.16 |
| 4,840,623 | 6/1989 | Quackenbush | 604/280 |
| 4,846,191 | 7/1989 | Brockway et al. | 128/748 |
| 4,864,464 | 9/1989 | Gonzalez | 361/311 |
| 4,869,718 | 9/1989 | Brader | 128/207.17 |
| 4,886,496 | 12/1989 | Conoscenti et al. | 604/96 |
| 4,898,163 | 2/1990 | George | 128/200.26 |
| 4,953,547 | 9/1990 | Poole, Jr. | 128/203.12 |
| 4,981,466 | 1/1991 | Lumbert | 604/19 |
| 4,981,470 | 1/1991 | Bombeck, IV | 128/635 |
| 4,981,477 | 1/1991 | Schon et al. | 604/264 |
| 4,995,384 | 2/1991 | Keeling | 128/207.18 |
| 5,031,613 | 7/1991 | Smith et al. | 128/207.14 |
| 5,054,482 | 10/1991 | Bales | 128/207.14 |
| 5,058,579 | 10/1991 | Terry et al. | 128/207.14 |
| 5,060,645 | 10/1991 | russell | 128/207.14 |
| 5,060,646 | 10/1991 | Page | 128/207.14 |
| 5,062,420 | 11/1991 | Levine | 128/204.18 |
| 5,067,496 | 11/1991 | Eisele | 128/207.15 |

FOREIGN PATENT DOCUMENTS

WO89/02761 4/1989 PCT Int'l Appl.

OTHER PUBLICATIONS

"The Micro-Trach: A Seven-Year Experience with Transtracheal Oxygen Therapy," Henry J. Heimlich et al., Chest, vol. 95, No. 5, (May 1989).
"Transtracheal Oxygen Therapy; A Guide for the Respiratory Therapist", Bryan Spofford et al., Respiratory Care, vol. 32, No. 5 (May 1987).

Primary Examiner—Edgar S. Burr
Assistant Examiner—Aaron J. Lewis
Attorney, Agent, or Firm—Workman Nydegger Jensen

[57] ABSTRACT

A multi-layered transtracheal catheter. The transtracheal catheter has a multi-layer or double wall construction formed of two materials. One material is resistant to kinking. The other material is resistant to mucous buildup. Together, they form a catheter that can remain within the trachea for an extended period of time without needing to be removed for cleaning.

36 Claims, 4 Drawing Sheets

5,218,957

MULTI-LAYERED TRANSTRACHEAL CATHETER

BACKGROUND

The Field of the Invention

This invention relates to medical catheters adapted for insertion into the trachea. More particularly, this invention relates to a multi-layered transtracheal catheter.

Review of Technical Background

Patients suffering from chronic oxygen-dependent respiratory failure must have an almost constant supply of oxygen. Today, many patients with chronic oxygen-dependent respiratory failure use nasal cannulas for their oxygen therapy. With nasal cannula therapy, patients receive needed oxygen through tubes which are attached to their nasal passages However, there are some disadvantages associated with nasal cannula therapy. One is that before the oxygen can reach the lungs, it must first pass through the nasal passages, the back of the mouth, and the vocal chords. By this route, much oxygen escapes from the mouth and the nose and is lost. There are two problems which result from this loss of oxygen. One is that the patient's oxygen saturation level is lower than it otherwise would be if the oxygen had not been lost. This makes it more difficult for the patient to exercise, and exercise is often an important component of recovery for such patients. A second problem is that since much of the oxygen is lost, patients are forced to carry with them larger containers of oxygen. For many, this is not only burdensome, but also immobilizing, particularly in the case of persons who may be seriously physically weakened due to age or illness.

An additional problem with the use of typical nasal cannula devices is discomfort. A constant flow of dry, cold oxygen in the nasal passages causes drying of delicate nasal membranes. This drying can cause the nasal passage tissues to swell and become sore. As a consequence, less oxygen is delivered through the swollen nasal passages making breathing more difficult so that frequently a patient will attempt to breathe through the mouth, which further complicates the matter. This problem is especially acute during the night when oxygen saturation levels are already at their lowest. In addition, because the nasal cannula is attached around the front of the face, pressure sores often appear on the tops of the user's ears. Also, a patient's face can become irritated by the plasticizers in the attachment strap. Because of these side effects of nasal cannula therapy, patients have been very reluctant to continuously wear such nasal cannula devices as prescribed. Thus, the effectiveness of the therapy is reduced.

Devices and methods have been developed which solve many of these problems. One such method, called transtracheal oxygen delivery, requires use of a small polytetrafluoroethylene catheter inserted into the trachea through the skin at the base of the neck. On the end of the catheter is attached a luer connector which connects the catheter to an oxygen source. With the use of this device, oxygen is neither lost nor wasted because it is delivered directly to the trachea. Thus, oxygen delivery is more efficient. Patients are more mobile because they are able to carry around smaller containers of oxygen, and because of better oxygen saturation.

This device and method also solve the problem of irritation of the nose and face. Since the oxygen no longer has to pass through the nose, the nasal tissues no longer become dry and irritated. Further, there is no longer any facial attachments to irritate or encumber the face and ears.

A further advantage of the transtracheal oxygen delivery device and method is the fact that it assists the patient in breathing. Breathing requires a certain amount of work. If a patient has chronic obstructive lung disease, the amount of work needed to breathe is increased. This work is reduced by the delivery of oxygen directly to the lungs by the pressure of the oxygen tank. Thus, with transtracheal oxygen delivery a patient is able to work less to get the same volume of oxygen to the lungs.

Although the transtracheal device and method solves many of the problems and disadvantages of nasal cannula therapy, some problems still remain. For example, some catheters devised for transtracheal oxygen delivery have been made of polytetrafluoroethylene.

Polytetrafluoroethylene appeared to be desireable because of its resistance to the mucous found lining the trachea, so that the mucous did not cling to the catheter. Mucous buildup on the transtracheal catheter causes primarily two problems. First, as the mucous begins clinging to and building up on the catheter, a ball may form which ultimately may become large enough to obstruct the trachea. A second, related problem is that even if the mucous does not build up to the point where it obstructs the trachea, at times the mucous may tend to slide to the end of the catheter and to build up at that point so that it will occasionally entirely close off and clog the end of the catheter opening. In either case, the result is obstructed and encumbered breathing capacity.

The resistance of polytetrafluoroethylene to the build up of mucous enabled polytetrafluoroethylene catheters to remain in the trachea for thirty days at a time without having to be removed for cleaning or replacement. Unfortunately, however, such polytetrafluoroethylene catheters would often kink within two to three weeks of placement. When a transtracheal catheter is placed in the trachea, it must be able to make an essentially ninety degree bend after the catheter passes through the neck of the patient so as to extend the end of the catheter down toward the lungs. If the catheter is not flexible enough and does not have sufficient circular memory and resiliency, certain kinds of abrupt action such as swallowing, turning the head, coughing and the like will tend to result in such kinking.

To avoid kinking, one solution appeared to be the use of urethane in forming the catheter rather than polytetrafluoroethylene. Urethane is a soft material with good characteristics of resiliency and circular memory that enable the catheter to resist kinking. It is also hypoallergenic. However, urethane is also hydrophilic, and is thus very susceptible to mucous buildup. As noted above, when mucous attaches itself to the catheter, it will typically form a ball and may clog either the opening of the catheter or the trachea. As a result, although urethane catheters res the tendency to kink, they typically have to be removed twice a day for cleaning.

An additional problem with transtracheal urethane catheter devices is that because of their softness, they tend to move about excessively with rapid inhalation or exhalation, such as experienced with coughing, sneezing, etc. This causes irritation of the trachea, and induces coughing.

BRIEF SUMMARY AND OBJECTS OF THE INVENTION

In view of the present state of the art, it is an object of the present invention to provide a transtracheal catheter of materials which will not only resist kinking, but will also be resistant to mucous buildup and attachment, thus permitting the catheter to remain in the trachea for extended periods of time.

Still another object of the present invention is to provide a transtracheal catheter that is soft and flexible enough to bend in order to be inserted into the trachea, but is not so soft and flexible that it moves excessively when rapid or abrupt inhalation or exhalation is experienced.

These and other objects and advantages of the invention will become more fully apparent from the description and claims which follow, or may be learned by the practice of the invention.

In accordance with the foregoing objects, the present invention is directed to a transtracheal catheter having a multi-layer or double wall construction formed of two materials. One material is resistant to kinking. The other material is resistant to mucous buildup. Together, they form a catheter that can remain within the trachea for an extended period of time (e.g., typically up to 30 days) without needing to be removed for cleaning.

One presently preferred method for manufacturing the transtracheal catheter of the present invention is by a coextrusion process. Two materials are coextruded to form a double walled catheter. The outer layer or wall is formed of a material which is hydrophobic, and not attractive to mucous. This material generally has a low coefficient of friction so that the mucous easily slides off. An example of an appropriate material is a polyamide-type material.

The inner layer or wall is formed of a more flexible material, such as urethane, that is resistant to kinking. This material, although it may be attractive to mucous, is protected from the mucous by the outer wall. The inner layer or wall is generally much thicker than the outer layer or wall so that the overall transtracheal catheter will be sufficiently resilient and supple to resist kinking, yet the outer wall will be sufficiently rigid and thick to provide sufficient rigidity so that the catheter will not move excessively in the event of abrupt or rapid inhalation or exhalation. The outer layer of material, chosen for its resistance to mucous and added rigidity, can be relatively thin. At the proximal end of the catheter a hub assembly is connected for attachment to oxygen and irrigation devices.

Although coextrusion has been found to be a successful method of forming the transtracheal catheter of the present invention, other methods can also be used. One method could be by dip coating a mucous resistant material over an inner wall formed of a material that is softer and more flexible.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode for making and using the invention will be described and explained with additional specificity and detail through the use of the accompanying drawings in which.

In the drawing figures, like parts have been designated with like numerals throughout.

DETAILED DESCRIPTION OF THE PREFERRED EMBODIMENT

Figure 1:
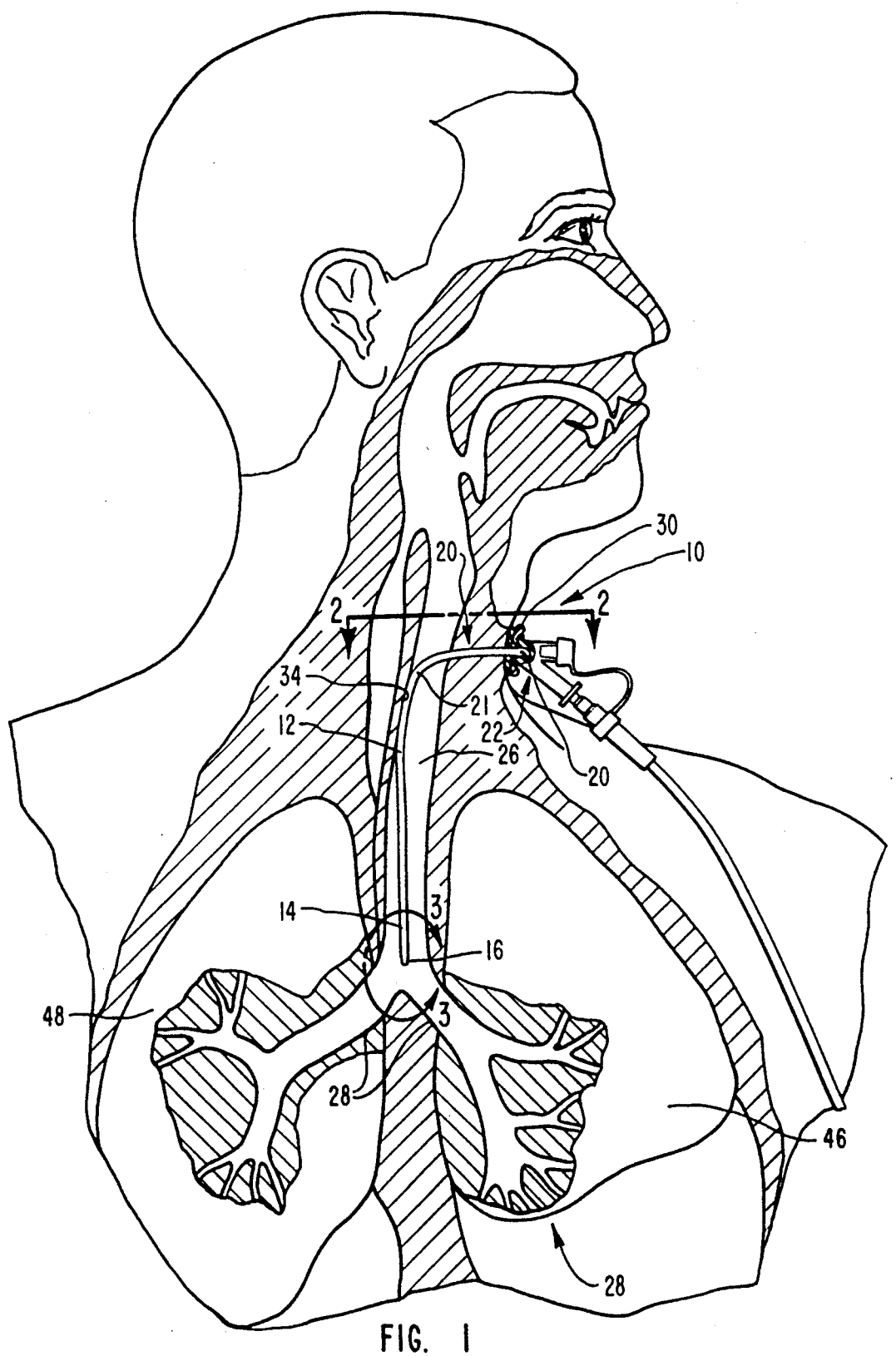
FIG. 1 is a perspective view of one presently preferred embodiment of the present invention illustrating the insertion of the transtracheal catheter into the trachea of a patient.
Figure 6:
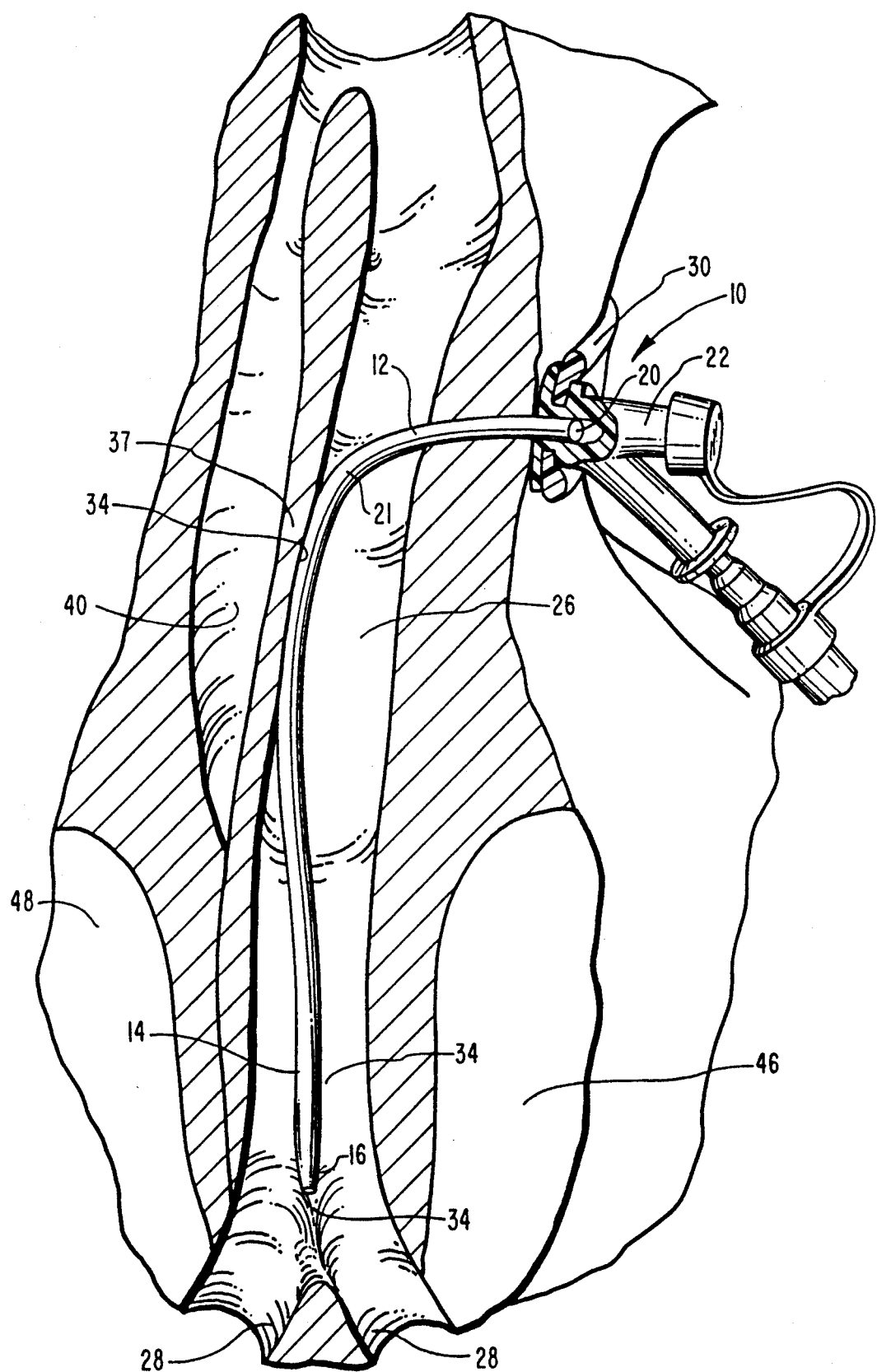
FIG. 6 is an enlarged perspective view with portions broken away particularly illustrating placement of the transtracheal catheter in a patient's trachea, and which illustrates how the transtracheal catheter is firmly held in place against the posterior wall of the trachea once in place.

Reference is first made to FIGS. 1 and 6 which illustrate the use of the present invention. The transtracheal catheter apparatus is generally designated at 10 and is comprised of an elongated catheter body 12 which terminates at its distal end 14 in a smoothly tapered tip 16, and which is attached at its proximal end 20 to a Y connector 22. Distal end 14 of the elongated catheter body 12 is smoothly tapered at tip 16, so as to minimize the possibility of damage to the trachea 26.

The catheter 10 is inserted into the trachea 26 through a small puncture made at the base of the patient's neck. Insertion at this position allows oxygen to be delivered directly into the trachea 26, ensuring that less or no oxygen is lost or wasted. Once the catheter 10 is inserted into the trachea 26, it bends at point 21 sharply downward, making an essentially 90° bend and being positioned such that it rests along the posterior wall 34 of the trachea. As illustrated best in FIG. 6, preferably the catheter body 12 will be firmly held against the posterior tracheal wall 34 from the point of bend 21 to the distal tip 16.

Figure 3:
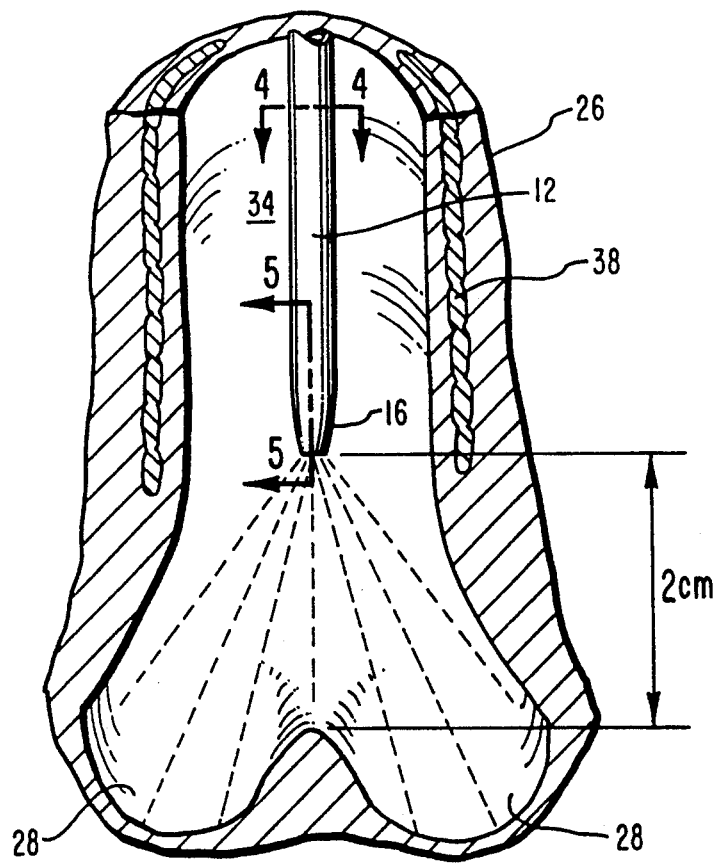
FIG. 3 is a cross-section taken along the line 3—3 of FIG. 1 and illustrating the placement of the catheter such that fluids emanating from the catheter evenly reaches the right and left lung.

As can be seen best from FIGS. 1, 3 and 6 taken together, the catheter 10 is long enough so that when it is inserted into the trachea 26 the tapered tip 16 will be positioned about two centimeters from the point where the left and right main stem bronchi 28 begin. As will be further described below, double wall construction of the elongated catheter body 12 is designed so that it has characteristics of stiffness, resiliency, suppleness and circular memory such that the elongated catheter body 12 will be gently curved as illustrated at the point 21 without kinking during use, and is yet stiff enough so that unwanted movement during rapid or abrupt inhalation or exhalation will be minimized in order to reduce or minimize irritation to the trachea.

Figure 2:
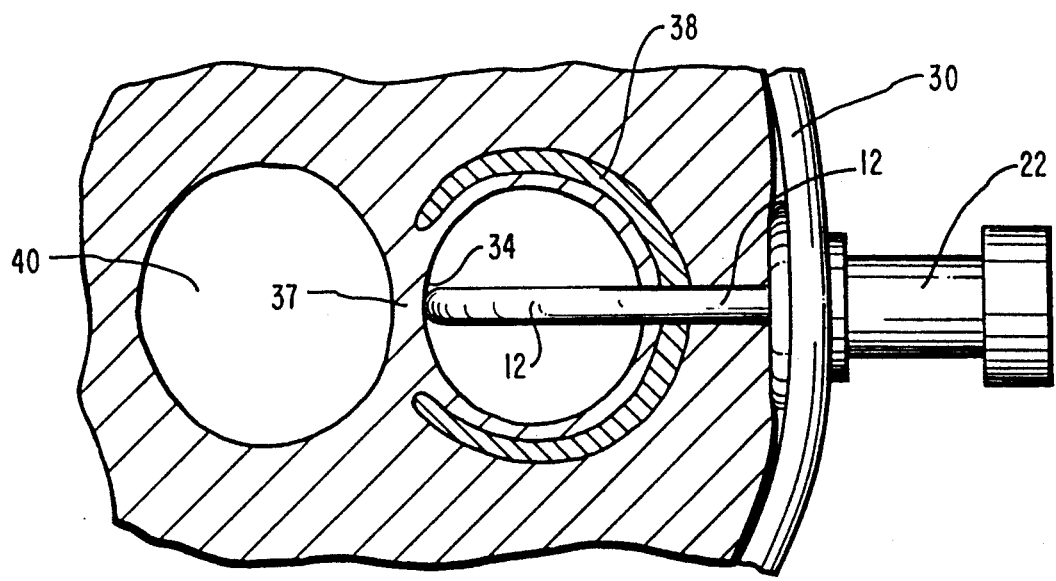
FIG. 2 is a cross-section taken along the line 2—2 of FIG. 1, illustrating the placement of the catheter against the soft membranous back wall of the trachea.

The posterior wall 34 of the trachea is made of soft membranous tissue. Around the sides and front of the trachea 26 are rigid rings 38 (see FIGS. 2 and 3). If a transtracheal catheter is positioned over these rigid rings 38, the catheter tends to cause irritation to the trachea. However, at the posterior wall 34 of the trachea, there are no rings, only the soft membranous tissue. When the catheter 12 of the present invention is placed within the trachea 26, it is thus preferably centered over the posterior wall 34. Because, as described further below, the outer wall 58 (see FIGS. 4 and 5) adds a degree of stiffness to the elongated catheter body 12, the catheter body 12 will tend to rest and be firmly held against posterior wall 34. The advantage of holding the catheter body 12 firmly against this wall 34 is that there is less sensation of movement since the posterior wall 34 is smooth, not ringed, resulting in less irritation and coughing. FIGS. 2 and 6 illustrate the positioning of catheter body 12 against the posterior wall 34. As can be seen, the catheter 12 does not puncture the wall 37 between the trachea and the esophagus 40. Catheter body 12 remains within the trachea 26, and follows the posterior wall 34 down to a point near the left and right main stem bronchi 28 (FIGS. 1, 3 and 6).

Referring now to FIG. 3, it can be seen that the catheter 12 is positioned so that the tapered tip 16 terminates about two centimeters from the area of branching of the right and left main stem bronchi 28. At this position, oxygen, saline medication or such fluids as are injected through the catheter 10 will tend to be sprayed evenly between the right and left lung.

Figure 4:
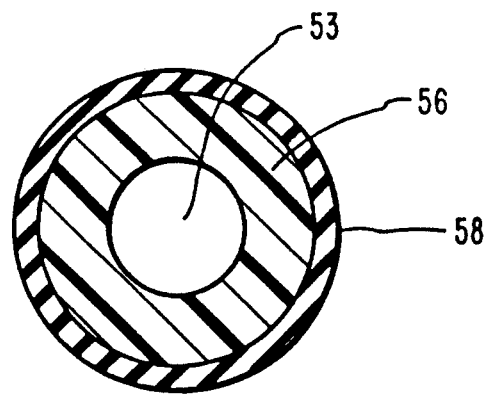
FIG. 4 is a cross-section taken along line 4—4 of FIG. 3, illustrating the double wall or multi-layered construction of the present invention.
Figure 5:
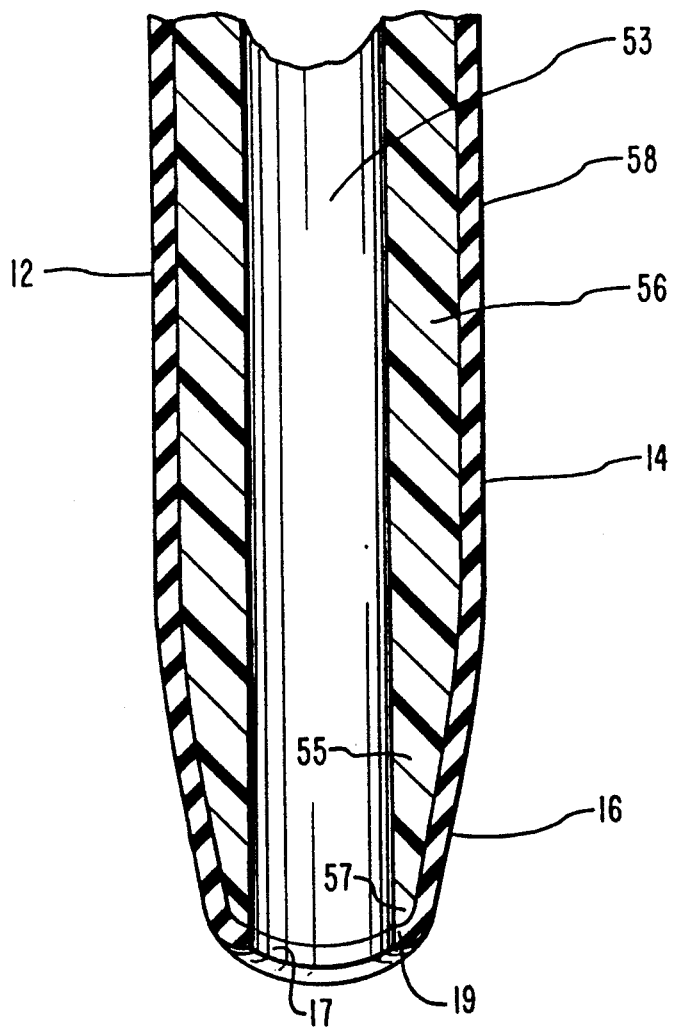
FIG. 5 is a cross section view taken along line 5—5 of FIG. 3, illustrating the inner and outer layers of the transtracheal catheter of the present invention, and its smoothly tapered tip.

FIGS. 4 and 5 are cross-sections of the distal end 14 of catheter 12. These figures illustrate an inner wall or layer 56 and an outer wall or layer 58 of which the catheter body 12 is comprised. Each wall or layer is comprised of a material which has specifically selected characteristics and each is designed with a relative thickness to achieve desired overall characteristics as described below.

Inner wall or layer 56 comprises, for example, a material which is soft and flexible enough so that it will bend, but not kink during prolonged use. The outer wall or layer 58 comprises a material that is hydrophobic and has a low coefficient of friction such that the mucous within the trachea does not adhere to the outer wall 58 and cause blockage of the opening 17 or trachea 26. The material of the outer wall 58 must be resistant to moisture and have a low coefficient of friction so that when mucous contacts the outer layer 58, it readily slides down the outer wall 58 and off the catheter 10.

The outer wall or layer 58 thus protects the catheter 10 against mucous buildup. As long as outer wall 58 covers all exposed areas of the catheter body 12, mucous buildup will be prevented. Accordingly, as shown best in FIG. 5, outer wall or layer 58 curves around and fully covers as shown at 19 the extreme end 57 of inner wall or layer 56, thus insuring that the inner wall 56 is completely isolated from mucous. Since oxygen is typically being injected essentially constantly through the catheter 10, mucous cannot migrate into the inner lumen 53 defined by the inner wall 56. Further, it is to be noted that inner wall or layer 56 tapers at 55 to form the gently tapered tip portion 16.

The outer layer 58 need not be very thick. In one preferred embodiment within the scope of the invention, the outer layer 58 is one-fourth the thickness of the inner layer 56. Generally the outer layer 58 need only be thick enough to cover the catheter body 12 to protect it from the mucous so that the catheter may stay in the trachea for a longer period of time without having to be often removed for cleaning, and/or to provide the desired degree of stiffness to prevent or minimize unwanted movement. Thus, outer layer 58 need only serve as essentially an exoskeletal member of the catheter body 12.

The inner layer 56 is preferably of a greater thickness. The purpose of this layer is to provide flexibility to the catheter so that it can bend yet not kink when placed in the trachea for long periods of time. The thickness of this inner layer 56 also provides the support for the catheter. Since the inner wall or layer 56 is entirely enclosed within the protective outer layer 58, it need not be hydrophobic and mucous resistant. It must only be soft, flexible, with good characteristics of resiliency and circular memory so as to be kink resistant. The respective widths of inner layer 56 and outer layer 58 can best be seen in FIGS. 4 and 5. In one presently preferred embodiment the outer wall is, for example, 0.003 inches in thickness, and is comprised of polyester block amide (PBAX TM), and the inner wall is 0.012 inches in thickness, and is comprised of urethane. Other possible materials from which outer wall 58 could be formed comprise polytetrafluoroethylene or polyethylene, or other polyamide-like materials. Other possible materials from which inner wall 56 could be formed include natural rubber or other flexible polymer or latex-type materials.

The inner and outer layers 56, 58 smoothly taper to a tip 16 at the distal end 14 of catheter 12. The tip 16 is smoothly tapered so that the catheter will not tend to damage the body tissues of the trachea 26. The tip 16 is also tapered gradually so that spray exiting from the catheter 10 is spread equally between the right and left lung. Again, as noted above, the outer layer 58 completely wraps around and covers the inner layer 56 as shown at 19 in FIG. 5 as a protection against mucous contact.

One method of manufacturing the catheter of the present invention is by co-extrusion processes such as are known in the art. An advantage of using this process is that the overall catheter diameter can easily be made smaller or larger as dictated by the needs of particular patients.

Another possible method of manufacturing the catheter of the present invention is by dipcoating catheters formed of flexible kink resistant material using material that is hydrophobic and resistant to the adherence of mucous. With this dipcoating method, the outer material need not be a material that is extrudable. For example polytetrafluoroethylene, a hydrophobic but not easily co-extrudable material, may be used in this way.

From the foregoing, it will be appreciated that a substantial advantage of the catheter apparatus of the present invention is that because of the materials of which the catheter body is comprised, and the specific characteristics of the materials of the outer and inner walls, the catheter can be left within the body for longer periods of time without kinking and/or mucous buildup. The catheter of the present invention also permits positioning within the trachea so that there is minimal unwanted movement and hence irritation of the trachea. An additional advantage of the catheter of the present invention is that it allows positioning such that the fluid being injected from the catheter is dispersed evenly between the right and left lung.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description, and all changes which come within the meaning and range of equivalency of the claims are to be embraced within their scope.

What is claimed is:

1. A transtracheal catheter comprising:
 an elongated catheter body comprising:
  an inner layer and means to resist kinking of said inner layer and including constructing said inner layer of a material that is soft and flexible to the extent that it will bend rather than kink when placed within a patient's trachea for extended periods of time; and
  an outer layer fused to the inner layer and comprising a material that is sufficiently hydrophobic and that has a sufficiently low coefficient of friction such that said outer layer is resistant to mucous buildup when placed in the trachea, said outer layer essentially completely covering said inner layer to prevent contact of mucous by the inner layer, and in combination with said inner layer provides said catheter body with enough softness and flexibility to bend rather than kink when placed within a patient's trachea for an extended period of time, and with enough rigidity to hold said catheter body firmly against a posterior wall of the trachea to minimize unwanted movement of the catheter body; and
 means for connecting said catheter body to an oxygen source.

2. A transtracheal catheter as defined in claim 1, wherein the material of said outer layer is a polyester block amide.

3. A transtracheal catheter as defined in claim 1, wherein the material of said outer layer is polytetrafluoroethylene.

4. A transtracheal catheter as defined in claims 2 or 3, wherein the material of said inner layer is urethane.

5. A transtracheal catheter as defined in claims 2 or 3, wherein the material of said inner layer is natural rubber.

6. A transtracheal catheter as defined in claims 1 or 4, wherein said inner layer has a first thickness, wherein said outer layer has a second thickness and wherein said outer layer adds rigidity to the overall catheter body, the relative thicknesses of said inner and outer layers being selected in relation to one another so that said catheter body will be rigid enough to be held against a patient's posterior tracheal wall to lessen unwanted movement of the catheter body.

7. A transtracheal catheter as defined in claim 6, wherein said outer layer is approximately one fourth the thickness of said inner layer.

8. A transtracheal catheter as defined in claims 1 or 4, wherein said outer layer is approximately one fourth the thickness of said inner layer.

9. A transtracheal catheter as defined in claim 1, wherein said catheter body is tapered at a distal end thereof.

10. A transtracheal catheter as defined in claim 9, wherein said inner layer is tapered in thickness at said distal end and said outer layer has a uniform thickness throughout the length of said catheter body.

11. A transtracheal catheter as defined in claim 1, wherein the material of said outer layer is polyethylene.

12. A transtracheal catheter as defined in claim 11, wherein the material of said inner layer is urethane.

13. A transtracheal catheter as defined in claim 11, wherein the material of said inner layer is natural rubber.

14. A transtracheal catheter comprising:
 an elongated catheter body defining an inner lumen therethrough and comprising:
  an inner wall and means to resist kinking of said inner wall and including constructing said inner wall of a material that is soft and flexible to the extent that it will bend rather than kink when placed within a patient's trachea for extended periods of time, and said inner wall having a first cross-sectional thickness; and
  an outer wall fused to the inner wall and comprising a material that is more rigid and less flexible than the material of said inner wall, said outer wall having a cross-sectional thickness which is less than the cross-sectional thickness of said inner wall but which, in combination therewith, provides said catheter body with enough softness and flexibility to bend rather than kink when placed within a patient's trachea for an extended period of time, and with enough rigidity to hold said catheter body firmly against a posterior wall of the trachea to minimize unwanted movement of the catheter body; and
 means for connecting said catheter body to an oxygen source.

15. A transtracheal catheter as defined in claim 14, wherein said material of said outer wall is also sufficiently hydrophobic and has a low enough coefficient of friction so that said outer wall is resistant to mucous buildup, and wherein said inner wall terminates at a point within said inner lumen and wherein said outer wall wraps around said inner wall at said point so as to essentially completely cover said inner wall to prevent contact of mucous by the inner wall.

16. A transtracheal catheter as defined in claim 14, wherein the material of said outer wall is a polyester block amide.

17. A transtracheal catheter as defined in claim 14, wherein the material of said outer wall is polytetrafluoroethylene.

18. A transtracheal catheter as defined in claims 16 or 17, wherein the material of said inner wall is urethane.

19. A transtracheal catheter as defined in claims 16 or 17, wherein the material of said inner layer is natural rubber.

20. A transtracheal catheter as defined in claim 14, wherein said outer wall is approximately one fourth the thickness of said inner wall.

21. A transtracheal catheter as defined in claim 14, wherein said catheter body is tapered at a distal end thereof.

22. A transtracheal catheter as defined in claim 21, wherein said inner wall is tapered in thickness at said distal end and said outer wall has a uniform thickness throughout the length of said catheter body.

23. A transtracheal catheter as defined in claim 14, wherein the material of said outer wall is polyethylene.

24. A transtracheal catheter as defined in claim 23, wherein the material of said inner wall is urethane.

25. A transtracheal catheter as defined in claim 23, wherein the material of said inner wall is natural rubber.

26. A transtracheal catheter comprising:

an elongated catheter body defining an inner lumen therethrough and comprising:

an inner wall and means to resist kinking of said inner wall and including constructing said inner wall of a material that is soft and flexible to the extent that it will bend rather than kink when placed within a patient's trachea for extended periods of time, and said inner wall having a first cross-sectional thickness; and an outer wall fused to the inner wall and comprising a material that is more rigid and less flexible than the material of said inner wall, said outer wall having a cross-sectional thickness which is less than the cross-sectional thickness of said inner wall but which, in combination therewith, provides said catheter body with enough softness and flexibility to bend rather than kink when placed within a patient's trachea for an extended period of time, and with enough rigidity to firmly hold said catheter body against a posterior wall of the trachea to minimize unwanted movement of the catheter body, and wherein said outer wall is also sufficiently hydrophobic and has a low enough coefficient of friction so that said outer wall is resistant to mucous buildup, and wherein said inner wall terminates at a point within said inner lumen and said outer wall wraps around said inner wall at said point so as to essentially completely cover said inner wall to prevent contact of mucous by the inner wall; and means for connecting said catheter body to an oxygen source.

27. A transtracheal catheter as defined in claim 26, wherein the material of said outer wall is a polyester block amide.

28. A transtracheal catheter as defined in claim 26, wherein the material of said outer layer is polytetrafluoroethylene.

29. A transtracheal catheter as defined in claims 27 or 28, wherein the material of said inner wall is urethane.

30. A transtracheal catheter as defined in claims 27 or 28, wherein the material of said inner layer is natural rubber.

31. A transtracheal catheter as defined in claim 26, wherein said outer layer is approximately one fourth the thickness of said inner layer.

32. A transtracheal catheter as defined in claim 26, wherein said catheter body is tapered at a distal end thereof.

33. A transtracheal catheter as defined in claim 32, wherein said inner wall is tapered in thickness at said distal end and said outer wall has a uniform thickness throughout the length of said catheter body.

34. A transtracheal catheter as defined in claim 26, wherein the material of said outer wall is polyethylene.

35. A transtracheal catheter as defined in claim 34, wherein the material of said inner wall is urethane.

36. A transtracheal catheter as defined in claim 34, wherein the material of said inner wall is natural rubber.

* * * * *

UNITED STATES PATENT AND TRADEMARK OFFICE
CERTIFICATE OF CORRECTION

PATENT NO. : 5,218,957
DATED : June 15, 1993
INVENTOR(S) : RICHARD D. STRICKLAND It is certified that error appears in the above-indentified patent and that said Letters Patent is hereby corrected as shown below:

```
Column 2, line 3, "attachments" should be --attachment--
Column 2, line 20, "desireable" should be --desirable--
Column 2, lines 35-36, "build up" should be --build-up--
Column 2, line 60, "res" should be --resist--
```

Signed and Sealed this

Twenty-ninth Day of March, 1994

Attest:

BRUCE LEHMAN

Attesting Officer

Commissioner of Patents and Trademarks